US009096984B2

(12) United States Patent
Somasundaran et al.

(10) Patent No.: US 9,096,984 B2
(45) Date of Patent: Aug. 4, 2015

(54) NETWORK MATERIAL DEVICES, METHODS, AND SYSTEMS

(75) Inventors: Ponisseril Somasundaran, Nyack, NY (US); Partha Patra, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 62 days.

(21) Appl. No.: 13/991,620

(22) PCT Filed: Dec. 6, 2011

(86) PCT No.: PCT/US2011/063596
§ 371 (c)(1),
(2), (4) Date: Jun. 4, 2013

(87) PCT Pub. No.: WO2012/078675
PCT Pub. Date: Jun. 14, 2012

(65) Prior Publication Data
US 2013/0273124 A1    Oct. 17, 2013

Related U.S. Application Data

(60) Provisional application No. 61/420,700, filed on Dec. 7, 2010.

(51) Int. Cl.
*E02B 15/04*    (2006.01)
*A61L 27/34*    (2006.01)
(Continued)

(52) U.S. Cl.
CPC ............... *E02B 15/041* (2013.01); *A61L 27/34* (2013.01); *A61L 27/54* (2013.01); *A61L 2300/62* (2013.01); *A61L 2300/802* (2013.01); *C02F 1/32* (2013.01)

(58) Field of Classification Search
USPC ............... 210/690–693, 502.1, 503, 505, 925
See application file for complete search history.

(56) References Cited

U.S. PATENT DOCUMENTS 2,907,682 A * 10/1959 Eichel .................. 428/317.3
6,039,901 A *  3/2000 Soper et al. ............... 264/4.3
(Continued)

FOREIGN PATENT DOCUMENTS

| WO | WO 2005/115603 A2 | 12/2005 |
|---|---|---|
| WO | WO 2009/070010 A1 | 6/2009 |
| WO | WO 2010/067904 | 6/2010 |

OTHER PUBLICATIONS

International Search Report and Written Opinion, dated Jun. 20, 2012, for International Application No. PCT/US11/63596.
(Continued)

*Primary Examiner* — Chester Barry
(74) *Attorney, Agent, or Firm* — Miles & Stockbridge P.C.; Mark A. Catan (57) ABSTRACT

Fibrillar bacterial proteins can be mixed with oil in or on water. The interaction of the proteins at the oil-water interface can result in oil dispersion in water in the form of droplets surrounded by an aggregated protein film. The film may be formed by multiple layers of the fibrillar proteins with water between adjacent protein layers. The proteins may be derived from bacterial cells, such as *Bacillus subtilis*. The encapsulated oil droplets can be collected from the water, for example, as part of an oil spill clean-up or oil storage. The oil may be removed from the collected droplets, for example, by evaporation to produce a three-dimensional network composed of the aggregated films. The three-dimensional network material can be used as a coating for transplant material, grafted onto implant material to improve biocompatibility, as a precursor for tissue growth or engineering, or provided into a human or animal body.

24 Claims, 7 Drawing Sheets

(51) Int. Cl.
 A61L 27/54 (2006.01)
 C02F 1/32 (2006.01)

(56) References Cited

U.S. PATENT DOCUMENTS

| | | | |
|---|---|---|---|
| 7,932,353 B2* | 4/2011 | van Es et al. | 530/356 |
| 2002/0028243 A1 | 3/2002 | Masters | |
| 2004/0124564 A1* | 7/2004 | Noorjahan et al. | 264/488 |
| 2009/0098600 A1* | 4/2009 | Uemori et al. | 435/69.1 |
| 2010/0203138 A1* | 8/2010 | Bouwstra et al. | 424/484 |
| 2010/0216708 A1 | 8/2010 | Jacobs et al. | |
| 2010/0233783 A1 | 9/2010 | Svensson et al. | |
| 2011/0306110 A1 | 12/2011 | Takeuchi et al. | |
| 2013/0256065 A1* | 10/2013 | Bongaerts et al. | 184/102 |

OTHER PUBLICATIONS

Das, Kishore et al., "Crude petroleum-oil biodegradation efficiency of *Bacillus subtilis* and *Pseudomonas aeruginosa* strains isolated from a petroleum-oil contaminated soil from North-East India," Bioresource Technology (2006) 1-7.

Haddad, Namir I.A. Haddad et al., "Identification of a Biosurfactant Producing Strain: *Bacillus subtilis* HOB2," Protein & Peptide Letters 16 (2009) 7-13.

Haghighat, S. et al., "Ability of indigenous *Bacillus licheniformis* and *Bacillus subtilis* in microbial enhanced oil recovery," Int. J. Environ. Sci. Tech. 5 (2008) 385-390.

Kim, Hee-Sik et al., "Production and Properties of a Lipopeptide Biosurfactant from *Bacillus subtilis* C9," J. Fermentation & Bioengineering 84 (1997) 41-46.

Miñana-Perez, Matilde et al., "Solubilization of polar oils with extended surfactants," Colloids and Surfaces A: Physicochemical and Engineering Aspects 100 (1995) 217-224.

Romero, Diego et al., "Amyloid fibers provide structural integrity to *Bacillus subtilis* biofilms," PNAS 107 (2010) 2230-2234.

Romero, Diego et al., "An accessory protein required for anchoring and assembly of amyloid fibres in *B. subtilis* biofilms," Molecular Microbiology 80 (2011) 1155-1168.

Suwansukho, Phitnaree et al., "Production and applications of biosurfactant from *Bacillus subtilis* MUV4," Songklanakarin J. Sci. Technol. 30 (Supp. 1) (2008) 87-93.

Pornsunthorntawee, Orathai et al., "Isolation and comparison of biosurfactants produced by *Bacillus subtilis* PT2 and *Pseudomonas aeruginosa* SP4 for microbial surfactant-enhanced oil recovery," Biochemical Engineering J. 42 (2008) 172-179.

Banat, I.M., "Biosurfactants production and possible uses in microbial enhanced oil recovery and oil pollution remediation: A review," Bioresource Technology 51 (1995) 1-12.

* cited by examiner

NETWORK MATERIAL DEVICES, METHODS, AND SYSTEMS

CROSS-REFERENCE TO RELATED APPLICATIONS

The present application is a U.S. national stage entry of International Application No. PCT/US11/63596, filed Dec. 6, 2011, which claims the benefit of U.S. Provisional Application No. 61/420,700, filed Dec. 7, 2010, all of which are hereby incorporated by reference herein in their entireties.

STATEMENT REGARDING FEDERALLY SPONSORED RESEARCH

This invention was made with government support under 1052697 awarded by the National Science Foundation. The government has certain rights in the invention.

FIELD

The present disclosure relates generally to protein-based films, and, more particularly, to encapsulation of oil droplets using extracellular bacterial proteins. Such encapsulation may be applied in various applications, including, but not limited to, oil dispersion/collection and containment, biocompatible coatings, and tissue growth and engineering.

SUMMARY

Systems, methods, and devices for forming and using network materials are disclosed herein. In general, extracellular proteins having a "fibrillar" morphology can be used to disperse oil in water. The aggregation of the proteins at the oil-water interface can disperse the oil into droplets, which are surrounded by a protein-aggregate film. The aggregate film may be formed by multiple layers of the fibrillar proteins with water disposed between the adjacent layers. The fibrillar proteins may be derived from cells, for example, extracellular reagents from Bacillus subtilis cells. The resulting aggregate films are strong and elastic such that oil droplets in the range of 50 nm to 2 mm are formed, with at least some droplets exceeding 1 µm in diameter. The encapsulated oil droplets can be collected from the water, for example, as part of an oil spill clean-up and/or for oil transportation and storage.

Additionally or alternatively, the oil can be removed from the collected, encapsulated droplets, for example, by evaporation to produce a three-dimensional network composed of the aggregate films. This three-dimensional network material can be used in a number of applications. For example, the fibrillar protein may be a human- or animal-biocompatible protein, such as fibronectin. The three-dimensional network material can be used as a coating for transplant material or grafted onto implant material to improve biocompatibility. The three-dimensional network material having micro-compartments or pockets therein can be used as a precursor for tissue growth or engineering and/or provided into a human or animal body, e.g., for cell or tissue growth.

In one or more embodiments, a method can include combining fibrillar proteins with oil such that the proteins form respective films encapsulating droplets of the oil. The method can further include, prior to the combining, collecting the fibrillar proteins from extracellular reagents of bacterial cells. The bacterial cells may include, for example, Bacillus subtilis. The collecting the fibrillar proteins can include purifying the collected proteins by isolating the fibrillar proteins from substantially globular proteins, for example, to a level of at least 60% fibrillar proteins by weight. The resulting oil droplets can have respective diameters in the range from 50 nm to 2 mm, with at least some of the oil droplets having diameters exceeding at least 1 µm. The oil droplets may be substantially aspherical. The oil may be disposed in a body of water, with the method including the collection of the oil droplets from the body of water. The method can also include evaporating the oil from the fibrillar proteins so as to leave a three-dimensional network material. The method can further include grafting the three-dimensional network material onto an implant or transplant, using the network material as a precursor for tissue or cell growth, and/or otherwise providing the network material into a human or animal body.

In one or more embodiments, a three-dimensional network material can include an aggregate film that has multiple layers of fibrillar proteins with a fluid between adjacent pairs of layer. The fluid can be water. The aggregate film can encapsulate a droplet of oil. The fibrillar proteins can include amyloidal fibers. The amyloidal fibers can be extracted from extracellular reagents produced by bacteria, for example, Bacillus subtilis. Alternatively or additionally, the fibrillar proteins can include fibronectin. The aggregate film can form one or more pockets, which may contain oil therein.

In one or more embodiments, a method for oil spill clean-up from a body of water using a network material can include selecting between a microbial entity that produces amyloids and amyloids that are isolated from the microbial entity. The method can further include adding the selected one to oil in the body of water such that the amyloids disperse the oil into droplets. Each of the droplets can be encapsulated by a respective aggregate film. Each aggregate film can include multiple layers of the amyloids with water disposed between adjacent layers. The oil droplets can have respective diameters in the range from 50 nm to 2 mm, with at least some having diameters of at least 1 µm. The oil can be crude oil. The microbial entity can include, for example, Bacillus subtilis. The method can further include culturing the microbial entity to a late stationary phase, harvesting and isolating the produced amyloids from the cultured microbial entity. The method can also include collecting the encapsulated oil droplets from the body of water. The collecting can involve using surface-modified hydrophobic nylon fibers to remove the encapsulated oil droplets. The method can include contacting the aggregate films together so as to form a three-dimensional network material with the oil droplets stored in pockets of the network material.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

DETAILED DESCRIPTION

Fibrillar proteins can be used to form a film that encapsulates oil (e.g., crude oil, hexane, or n-hexadecane) in an aqueous solution (e.g., water). The fibrillar proteins can be added to water with oil floating thereon and mixed (e.g., via mechanical agitation). The resulting interaction between the proteins and the oil can cause the proteins to assemble along the oil-solution interface to form the encapsulating film. The film may be formed by multiple layers of the fibrillar proteins with water disposed between the adjacent layers. The fibrillar proteins may be derived from cells, for example, extracellular reagents from *Bacillus subtilis* cells. Oil droplets encapsulated by the protein-based films can be relatively strong and elastic so as to survive subsequent handling (i.e., removal from the aqueous solution) or otherwise disperse the oil in the aqueous solution. Moreover, such films can be stable under typical atmospheric conditions (i.e., 25° C., 1 atm pressure) for more than an hour and have considerable elastic properties, as discussed further herein. The oil droplets can range in size from 50 nm to 2 mm, with at least some of the droplets exceeding 1 µm in diameter. Many of the oil droplets may actually exceed 1 µm in diameter. The encapsulated oil droplets can be collected from the water, for example, as part of an oil spill clean-up or oil storage.

In one or more embodiments, aqueous solutions containing a certain type of microbial entities can be added to oil in varying proportions. For example, the oil to aqueous solution ratio can be from 0.25:1 to 1:1 on a volume/volume basis. The aqueous solution can include bacterial cells as well as extracellular bacterial reagents and/or extracellular proteins. For example, concentrated bacterial cells (e.g., $5\text{-}8 \times 10^9$ cells/ml) can be obtained at a late stationary phase (e.g., 78 hours). The bacterial cells can be mixed with oil (e.g., n-hexadecane oil) in aqueous solution. As soon as the bacterial suspension is added to the oil phase, the oil phase may separate out of the aqueous solution as a distinct separate phase atop the aqueous solution. The solution can be agitated in order to enable the proteins and the bacterial cells to accumulate at the oil-water interface. For example, the solution can be agitated by mixing with a vibrator for seven days. After agitation, the oil phase may be dispersed in the aqueous phase, resulting in a substantially single phase with a relatively less distinguishable oil phase. This may be further indicative of effective oil dispersion.

Figure 1:
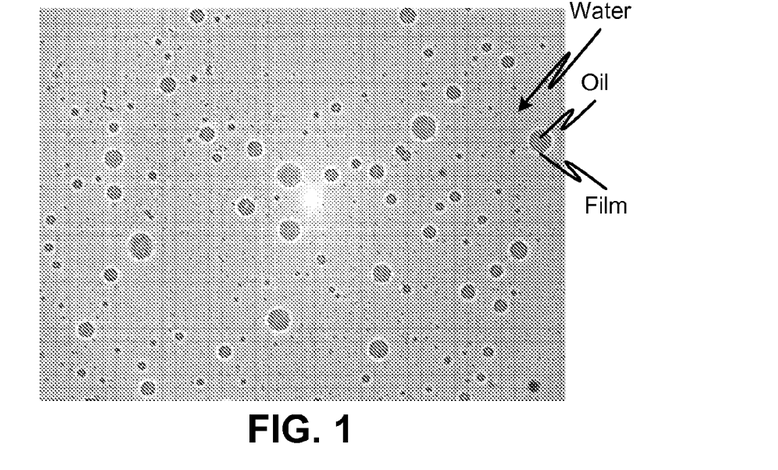
FIG. 1 is a phase-contrast microscope image at 2000× magnification of an aqueous phase after seven days of mixing bacteria with n-hexadecane oil, according to one or more embodiments of the disclosed subject matter.
Figure 2:
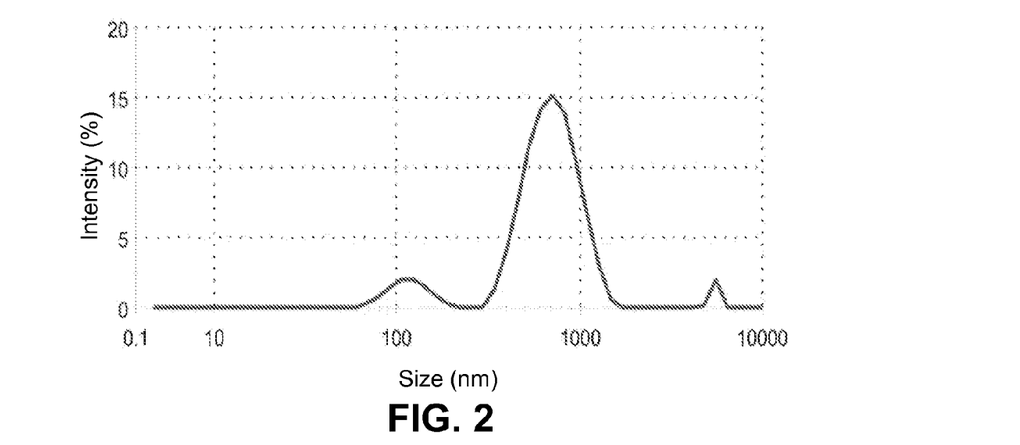
FIG. 2 is a graph showing oil droplet size distribution in the aqueous phase after seven days of mixing bacteria with n-hexadecane oil, according to one or more embodiments of the disclosed subject matter.

FIG. 1 shows a phase-contrast microscope image of oil droplets in the aqueous phase after seven days of vibrator mixing. In particular, the proteins produced by the bacteria aggregate at the oil-water interface resulting in oil droplets within the aqueous phase (e.g., water). As is evident from FIG. 1, droplets of various sizes are produced by the aggregation of the fibrillar proteins at the oil-water interface. The oil-dispersed aqueous phase can be centrifuged to isolate the oil droplets from the bacterial cells for further investigation. For example, the oil-dispersed aqueous phase can be centrifuged at 7000 rpm and the supernatant isolated for analysis. An exemplary size distribution for n-hexadecane oil droplets formed by mixing with the bacteria is shown in FIG. 2. As is apparent from FIG. 2, oil droplets as small as 60 nm and a large as 5 µm were produced, with at least some (e.g., many) of the droplets being greater than 1 µm in diameter.

Figure 3:
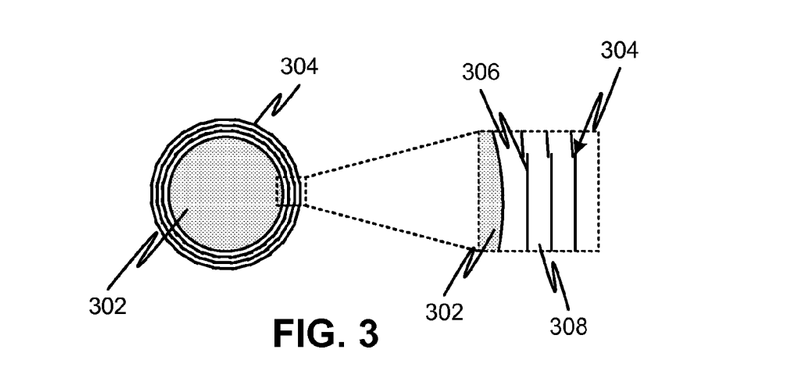
FIG. 3 is a schematic diagram of an oil droplet encapsulated by an aggregate film and a inset showing a close-up diagram of the film, according to one or more embodiments of the disclosed subject matter.

Referring to FIG. 3, a schematic diagram of an oil droplet shows film 304 encapsulating the oil droplet 302. The film 304 can include numerous protein-based films, for example, in the form of layers 306. The layers 306 may entrap the aqueous solution (e.g., water 306) therebetween within the film 304. This configuration may improve the structural stability and elasticity of the film 304, thereby allowing the droplet 302 to be encapsulated stably and reliably. The stability of the oil droplet within the aqueous solution may be on the order of 1 month or more.

Alternatively or additionally, fibrillar proteins in the extracellular bacterial reagents produced by the bacterial cells can be isolated and added to oil to produce the desired effect. Since the bacteria used to produce the results of FIG. 1 were in the late stationary phase, certain types of hydrophobic domain-based proteins may be responsible for formation of the encapsulating film. Amyloidal-type fibers that bear hydrophobic characteristics are present in biofilm produced by certain bacteria, for example, *Bacillus subtilis*. For example, *Bacillus subtilis* cells can be left in aqueous solution (e.g., de-ionized and/or distilled water) for a predetermined time period (e.g., 1 week). After the time period, the bacterial cells may be separated from the aqueous solution leaving behind the fibrillar proteins. The mixing of the aqueous solution having the proteins therein with oil can produce effects similar to those illustrated in FIG. 1.

Figure 4A:
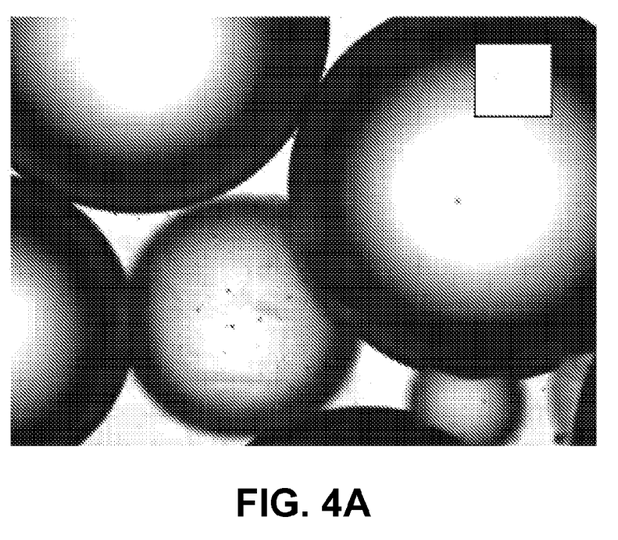
FIGS. 4A-4C are microscope images at 4000× magnification of collected, encapsulated oil droplets at a time of 0, 30 minutes, and 120 minutes, respectively, after exposure to air, according to one or more embodiments of the disclosed subject matter.
Figure 4B:
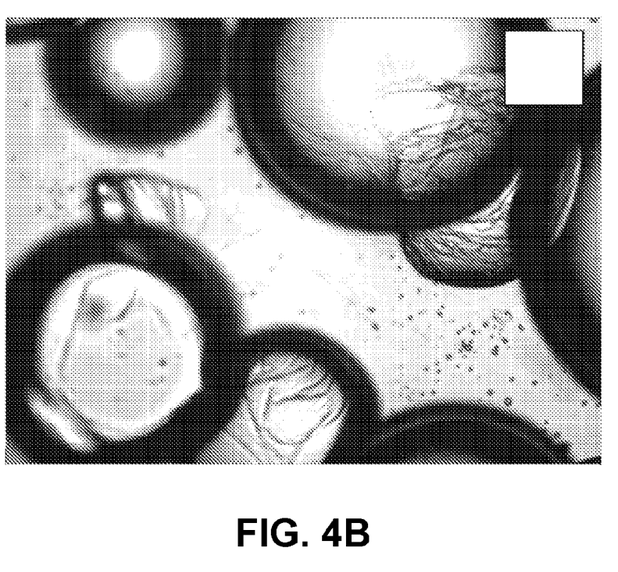
Figure 4C:
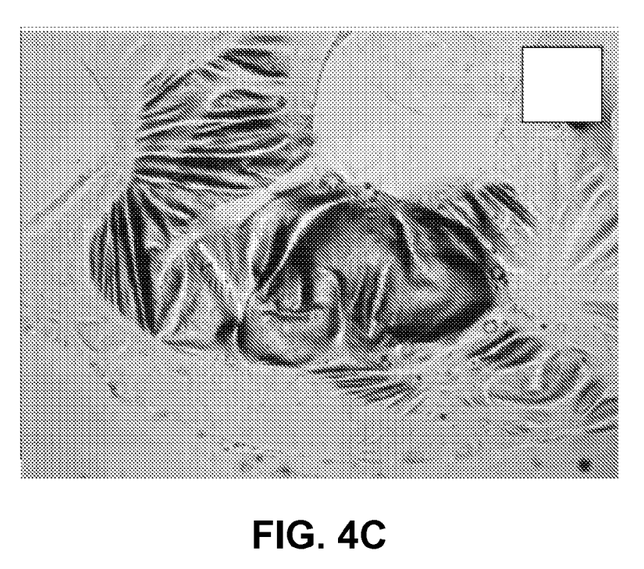

FIGS. 4A-4C shows phase-contrast microscope images of encapsulated oil droplets removed from the aqueous solution. A concentrated bacterial suspension was allowed to develop a film over oil for a seven day period, after which the cells were removed by centrifuging. The cell-free supernatant (i.e., containing substantially the fibrillar proteins) was mixed with the oil and agitated to allow the extracellular components to come interact with the oil. A layer of oil droplets may appear in the top oil phase and can be collected for removal from the aqueous solution. The droplets were removed using a wide mouth pipette tip and placed on a glass slide for observation in atmosphere under a phase contrast microscope. However, other collection and removal techniques are also possible, especially outside of the laboratory setting.

Figure 4D:
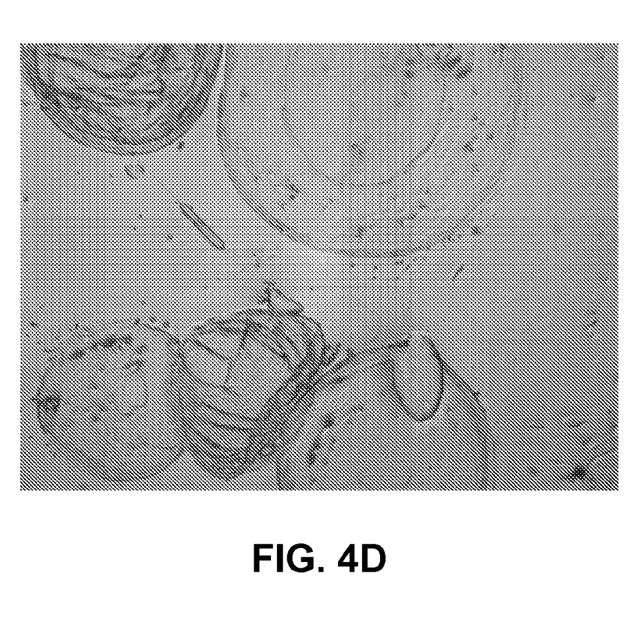
FIG. 4D is a microscope image at 4000× magnification of collected, encapsulated oil droplets that have collapsed after evaporation of the oil therein, according to one or more embodiments of the disclosed subject matter.

As shown in FIGS. 4A-4C, a protein film was formed on the oil droplets, which eventually collapses and/or ruptures as oil (e.g., n-hexadecane and/or hexane) evaporates upon exposure to atmosphere. After 120 minutes (i.e., FIG. 4C), with evaporation of water a thin layer of film can be found floating on the oil surface. Another example is shown in FIG. 4D, where hexane oil was used. Hexane has a relatively low boiling point (i.e., 50-60° C. at atmospheric pressure) and thus may readily evaporate from the oil droplets. As can be seen in FIG. 4D, the encapsulating film collapsed within a few minutes of exposure to atmosphere due to the evaporation of oil from therein. The film thus crumbles when oil is released therefrom that would otherwise be stabilized within the droplet via mechanical support of the film.

The fact that a film structure formed substantially of proteins remains after removal of the oil from the film allows the possibility for the film structure to be used for other applications. For example, the oil can be removed from the collected, encapsulated droplets, for example, by evaporation to produce a three-dimensional network composed of the aggregate films. This three-dimensional network material can be used in a number of applications. For example, the fibrillar protein may be a human- or animal-biocompatible protein, such as fibronectin. The three-dimensional network material can be used as a coating for transplant material or grafted onto implant material to improve biocompatibility. The three-dimensional network material can be used as a precursor for tissue growth or engineering or otherwise provided into a human or animal body. Other applications are also possible according to one or more contemplated embodiments.

Other fibrillar hydrophobic proteins than the bacteria-derived amyloidal fibers can also be used for oil droplet encapsulation for oil capture (e.g., oil dispersion or environmental remediation) and/or for construction of a protein-based three-dimensional network material. For example, fibronectin has a molecular morphology of a fibrillar nature. As various hydrophobic domains exist in the fibronectin molecules, it can be considered a surface active agent, allowing it to be used as an oil dispersant especially with regard to self-assembly of the fibronectin molecules at the oil-water interface. Oil (e.g., n-hexadecane) can be mixed with 0.05% of fibronectin solution in a mixing ratio of 1:1, v/v %. As shown in FIGS. 5A-5E, the fibronectin may form an encapsulating film that disperses the oil into stable droplets. The oil droplets may be of irregular shape as shown in FIGS. 5A-5E.

Oil can be stabilized/emulsified in water using surface active agents (surfactants). Oil can be either trapped in micelles of the surfactant or shaped as spherical oil droplets stabilized in water by the surfactant at the oil-water interface. While fibronectin may be considered a surfactant due to its hydrophobic domains, the irregular (e.g., aspherical) shape of the resulting oil droplets in water suggests that a different mechanism than typical surfactant mechanisms may be at work. Oil droplets stabilized by surfactants are generally spherical. For example, oil droplets formed using a protein such as bovine serum albumin (BSA) and keratin result in spherical oil droplets.

Figure 5A:
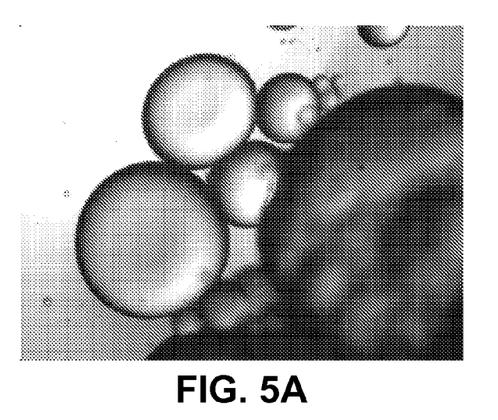
FIGS. 5A-5E are microscope images at 2000× magnification of n-hexadecane oil droplets encapsulated by fibronectin film at a time of 5 minutes, 60 minutes, 180 minutes, 240 minutes, and 400 minutes, respectively, after exposure to air, according to one or more embodiments of the disclosed subject matter.
Figure 5B:
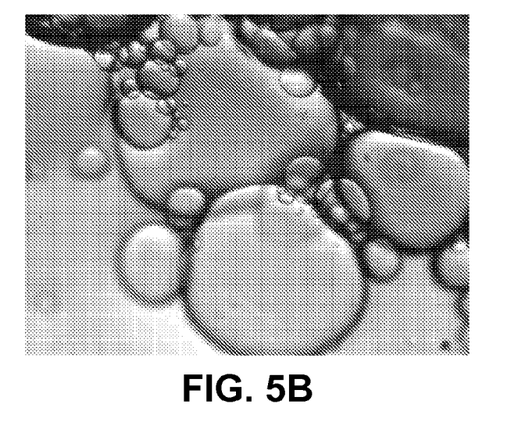
Figure 5C:
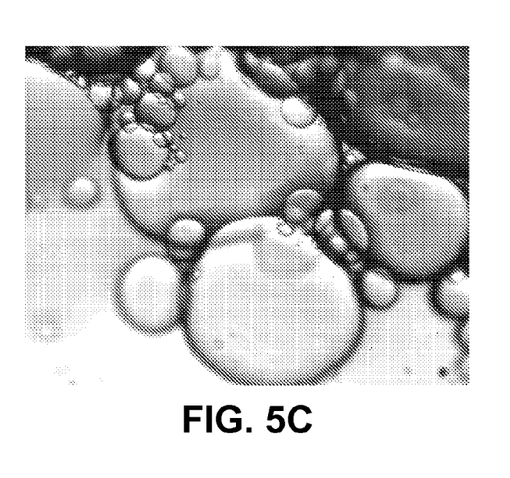
Figure 5D:
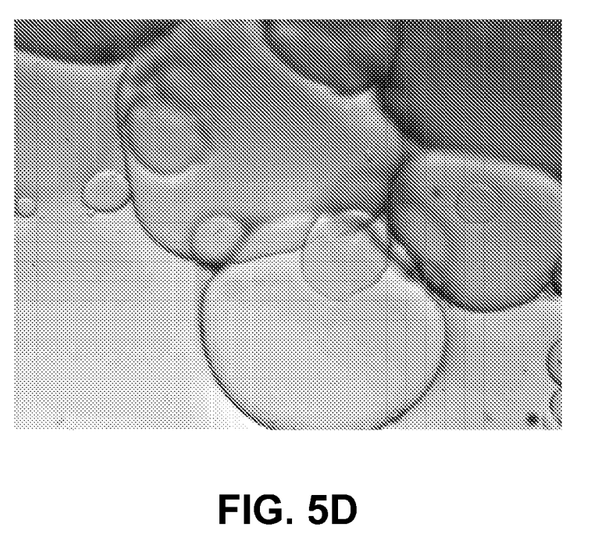
Figure 5E:
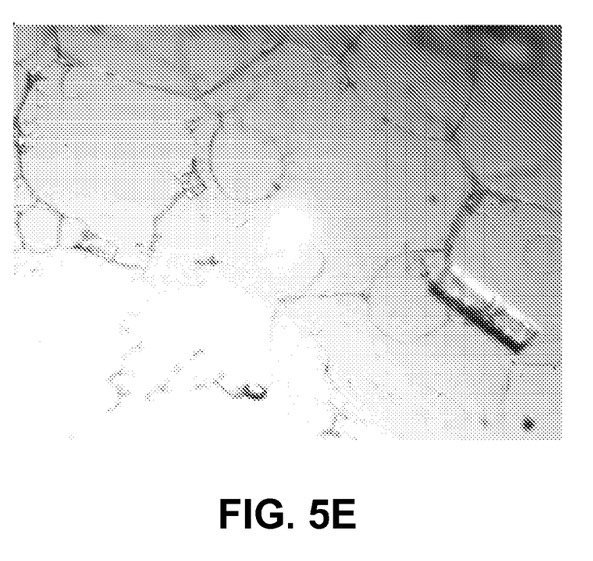
Figure 6:
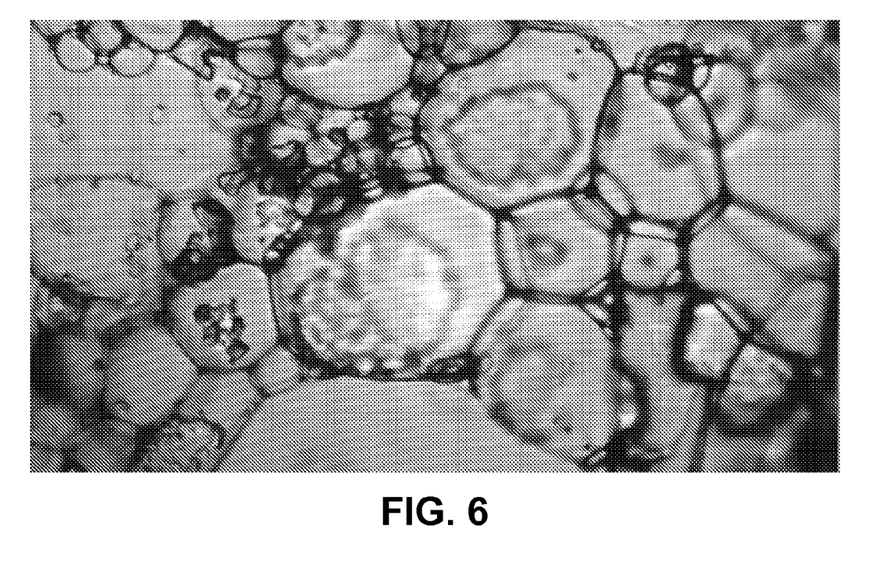
FIG. 6 is a microscope image showing a three-dimensional network material formed from fibronectin film with pockets containing n-hexadecane oil, according to one or more embodiments of the disclosed subject matter.

As with the bacteria-derived proteins, the film may collapse upon evaporation of the oil, as shown in FIG. 5E. However, the films remain resilient and are capable of withstanding forces without breaking. The fibronectin films can encapsulate n-hexadecane oil into droplets having sizes as large as 1-2 mm. The droplets can be removed from solution for further investigation and/or use (i.e., to form a three-dimensional network material). For example, FIG. 6 shows the oil droplets removed from solution and placed on a glass slide for 1-2 hours in atmosphere. The droplets may initially contact each other and coalesce to form a three-dimensional network material. The three-dimensional structure with pockets, which may hold or formerly have held oil therein, is apparent from the figure.

Such a network material has sufficient strength and capacity to hold relatively high viscosity oil, such as that of n-hexadecane. Moreover, this particular type of protein is naturally occurring in human and/or animal bodies, such that the material may be inserted into the living beings without damage or potential for bio-incompatibility. This network material may be used to improve the bio-compatibility of other materials or find other biological applications, such as, but not limited to, a scaffold or precursor for tissue engineering or growth.

Attenuated total reflectance Fourier transform infrared spectroscopy (ATR-FTIR) was used to examine the structure of inclusion bodies, folding aggregates, amorphous precipitates and amyloid fibrils of the three-dimensional network material. In particular, fibronectin self-assembled aggregate film at the oil-water interface of the droplets was interrogated using ATR-FTIR. For example, 0.1% (by weight) of human plasma fibronectin can be dissolved in 1 M Tris buffer solution and further diluted to 0.05% using nanopure water with conductivity of 18.1 Ω. 500 μl of 0.05% solution of the diluted fibronectin solution can be added to 500 μl of a mixture of oils (e.g., hexane and n-hexadecane at 1:1 v/v). With regard to the n-hexadecane, the oil may be observed as a separate phase over the fibronectin solution. The two solutions can be allowed to mix by gentle agitation, for example, shaking by a vibrator. Droplets may be observed toward the middle of the mixed solution and can be removed using, for example, a pipette for observation and/or use.

ATR-FTIR scans can be taken in a range from 4000 cm$^{-1}$ to 400 cm$^{-1}$, for example, on the three-dimensional network as it is collapsing or after it has collapsed due to removal (e.g., evaporation) of the oil therefrom. The lower ATR-FTIR traces in FIG. 7 were taken shortly after removing the oil droplets from solution. Observation of the fibronectin film by the ATR-FTIR scan is thus not possible. However, after evaporation of water and/or oil from the film over time, the concentration of fibronectin in the film increases and the ATR-FTIR was sufficiently sensitive to register a peak for fibronectin, represented by the upper ATR-FTIR traces in FIG. 7.

Figure 7:
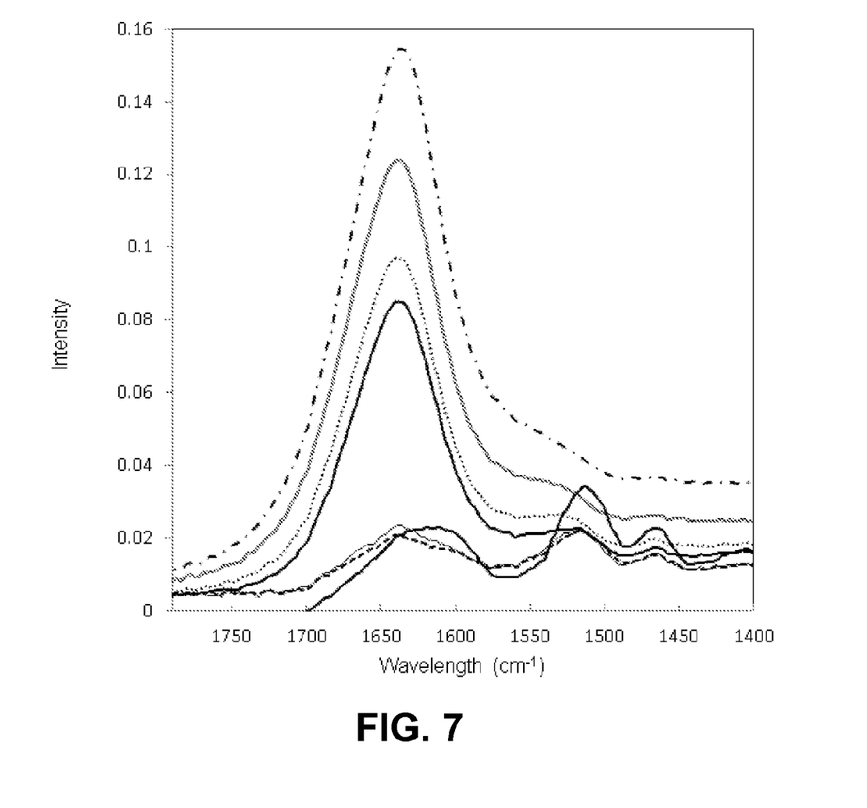
FIG. 7 is a graph showing attenuated total reflectance Fourier transform infrared spectroscopy (ATR-FTIR) results for the film encapsulating oil droplets at various times during the evaporation of the oil therein, according to one or more embodiments of the disclosed subject matter.

Amide I is the most intense absorption band of the polypeptides. The band for amide I is positioned at around 1600 cm$^{-1}$ (e.g., 1640 cm$^{-1}$), but its exact frequency is determined by the geometry of the polypeptide chain and hydrogen bonding. The band present around 1540 cm$^{-1}$ is the amide II contribution. The aggregates of fibronectin molecules are films of varying sizes, and the films align layer-wise. The ATR-FTIR spectra of the film encapsulating the oil droplet were continuously sampled during dehydration. Removal of the water was indicated by the O-H vibration peak at approximately 1600 cm$^{-1}$. This indicates that water was bound together with the proteins in the film. Thus, these layered films contain water between the films and can be thought of as protein-bound water, as shown in the inset of FIG. 3. The ATR-FTIR scans further demonstrate that the films encapsulating the stable oil droplets were indeed protein-based films, i.e., in this case, fibronectin films.

According to the teaching of the present disclosure, the protein-based coatings disclosed herein can be used as an oil dispersant or collection tool, for example, for oil spill cleanup or contamination remediation. Regarding oil spill applications, oil leaked over time after an oil spill may spread to various zones, such as the sea surface, the sub-sea region, and the deep sea region, as well as sensitive land areas, such as marshes, wetlands, and beaches. The use of conventional surfactants to disperse oil floating in water has generated concern regarding toxicity and negative impacts on the ecosystem. In contrast, the protein-based films described herein may enjoy improved biocompatibility and minimize or at least reduce the negative impacts on the ecosystem.

Figure 8:
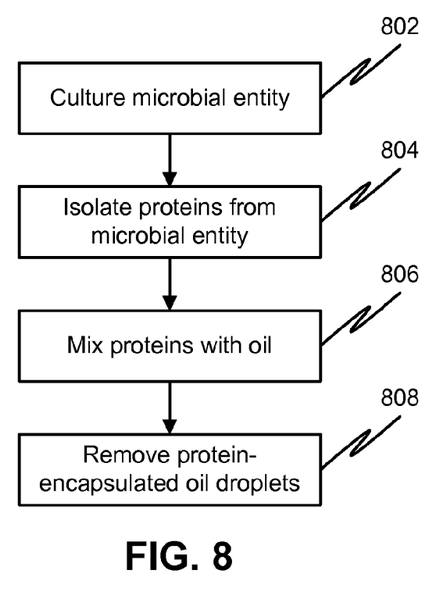
FIG. 8 is a simplified flow diagram of an exemplary process for removing oil from water, according to one or more embodiments of the disclosed subject matter.

An exemplary method for employing the aggregate films for oil spill clean-up is illustrated schematically in FIG. 8. At 802, a microbial entity may be cultured in order to produce one or more fibrillar and/or amyloid-type fibrillar proteins. The proteins may be located in extracellular reagents produced by the microbial entity. For example, the microbial entity can be *Bacillus subtilis*. For example, the microbial entity may be cultured in solution for a week, after which time the method can proceed to 804.

At 804, the proteins can be isolated from the microbial entity. For example, the solution containing the proteins and the microbial entities can be centrifuged. The substantially cell-free supernatants containing the proteins may be collected for further use. Alternatively, the microbial entities may be used together with the proteins as the oil dispersant in 806. Step 804 can also include purifying the proteins isolated from the microbial entities. The self-assemble nature of the protein films allows lower purity protein solutions to be used without significant negative impact. In other words, purification at the molecular level may not be necessary for the solution to be effective as an oil dispersant. For example, the desired proteins may be purified from the solution using conventional ammonium sulfate precipitation techniques. The resulting purified protein may be as little as 50-60% pure by weight. The method can proceed to 806.

At 806, the solution containing the fibrillar proteins can be mixed with oil in or on water to form oil droplets encapsulated by an aggregate film. When the water is a natural body of water, the wave action of the water may serve to mix the proteins and the oil together to form the oil droplets. When the water is a stagnant body of water, additional mechanical actuation of the water may be used to mix the proteins and the oil together. As a result of 806, the oil is dispersed into oil droplets suitable for subsequent capture and/or containment at 808. The aggregate film may serve to stabilize the dispersed oil in the water.

Hydrophobic fibers may be used for removal and recovery of the oil droplets. For example, the oil droplets may be selectively entrapped in hydrophobic fibers in flotation pulp followed by recovery as a froth phase. For example, relatively fine (i.e., having an aspect ratio of at least 1000) nylon fibers can be used for selective removal and recovery of oil from water. Furthermore, surface modification of the nylon fibers upon beating in grinding may lead to an increase in recovery of oil. A network of nylon fibers can be removed from suspension by the swarm of oil droplets in flotation. Of course, other approaches are also possible for application in oil-spill clean-up depending on the role they might play in specific zones. For example, other types of collection mechanisms may include, but are not limited to, wheel skimmers.

According to the teaching of the present disclosure, the protein-based coatings disclosed herein can be used as three-dimensional network materials, for example, for biological applications. An exemplary method for forming the three-dimensional network material is illustrated schematically in FIG. 9. At 902, an aqueous solution containing fibrillar proteins can be mixed with oil to form oil droplets encapsulated by an aggregate film formed of the fibrillar proteins. Mechanical agitation of the aqueous solution may be used to mix the oil and the proteins. As noted above, the aggregate film includes a plurality of layers of the fibrillar proteins with the aqueous solution interposed between adjacent layers. The method proceeds to 904.

Figure 9:
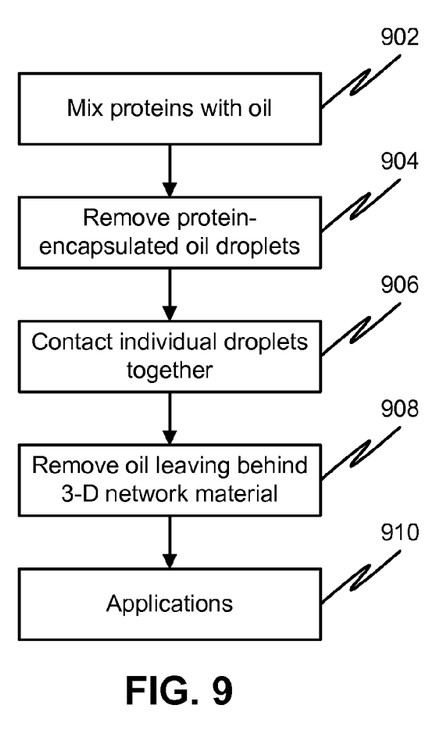
FIG. 9 is a simplified flow diagram of an exemplary process for forming and using a three-dimensional network material, according to one or more embodiments of the disclosed subject matter.

At 904, the encapsulated oil droplets can be removed from the aqueous solution. For example, the removed oil droplets can be retained in air or provided to another solution. Proceeding to 906, the removed oil droplets are brought into contact with each other such that the aggregate films of the oil droplets touch, but the oil contained therein remains separate. Over time, the aggregate films can merge together to form a three-dimensional network material with pockets therein. The pockets, corresponding to the oil droplet interior volume, may continue to hold the oil therein. The method thus proceeds to 908.

At 908, the oil within the pockets of the three-dimensional network material can be removed. For example, the oil may leave the network material via evaporation. In another example, the oil may be removed from the network material via sublimation or critical point drying. The three-dimensional network material remains behind and maintains its structure, albeit in a collapsed form. The resulting structure consists essentially of fibrillar proteins and/or the aqueous solution and can be used for a variety of applications at 910.

With respect to the applications at 910, the network material may enjoy mechanical features that may be advantageous for use in protein-based networks in cell biology, as a precursor structure for tissue repair and cell generation, in increasing generation of neuron cells, in control of amyloidal fibers in Alzheimer diseases and amyloidal-based liaisons in stomach, and in nanoparticles in biological membranes interactions for nanomedicine applications, as well as potentially lead to new tools for biomedical research. Other applications include biophysical systems, for example, the formation of extracellular matrix (e.g., fibronectin-based extracellular matrix) in living beings and methods for oil dispersion. The network material may also be applied to various processes in biological systems or for coatings in human transplant materials. A three-dimensional network material of fibronectin (or other biocompatible fibrillar protein) can be grafted onto implant material to improve the biocompatibility of the implant material. The three-dimensional network material of fibronectin (or other fibrillar protein) can be used as a precursor for tissue repair and growth or as a filling material for cell growth in, for example, surgery-based cancer treatment. In still another example, proteins solutions can be used to interact with oil to store oil in the pockets of the three dimensional network and to prevent or at least reduce oil evaporation which may contribute to air toxicities. The three dimensional network can also be used for drug delivery, nanoparticles in biological systems, or as a model biological tool to study growth and properties of stem cells. The above listing of applications for the three-dimensional network material is not intended to be exhaustive. Rather, many other applications are also possible according to one or more contemplated embodiments of the disclosed subject matter.

Although particular configurations have been discussed herein, other configurations can also be employed. Moreover, although specific microbial entities, proteins, and/or chemicals have been discussed, other microbial entities, proteins and/or chemicals may be used to achieve the desired effect. For example, the use of other fibrillar proteins besides fibronectin is also possible according to contemplated embodiments of the disclosed subject matter. In another example, other aqueous solutions besides water can be used according to contemplated embodiments of the disclosed subject matter.

All chemicals, compositions, and microbial entities described herein are for illustration purposes only and should not be understood as limiting of the embodiments of the disclosed subject matter. Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, network material devices, methods, and systems. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method comprising:
    combining fibrillar proteins with oil such that the proteins form respective films encapsulating droplets of the oil, wherein the fibrillar proteins include fibronectin, fibronectin-type long protein molecules, or amyloid-type fibers.

2. The method of claim 1, further comprising, prior to said combining, collecting the fibrillar proteins from extracellular reagents of bacterial cells.

3. The method of claim 2, wherein said bacterial cells include *Bacillus subtilis*.

4. The method of claim 2, wherein said collecting includes purifying the collected proteins by isolating the fibrillar proteins from substantially globular proteins.

5. The method of claim 4, wherein the purifying results in at least 50% fibrillar proteins by weight.

6. The method of claim 1, wherein the oil droplets have respective diameters in the range from 50 nm to 2 mm.

7. The method of claim 1, wherein the combining is such that fibrillar proteins encapsulate the oil droplets at an oil-water interface.

8. The method of claim 1, wherein:
    the combining includes mechanically agitating the proteins and the oil,
    the oil is in water and said agitating is provided at least in part by movement of the water, and
    said water is a naturally occurring body of water and said movement includes waves in the body of water.

9. The method of claim 1, further comprising, removing the droplets of oil such that a three-dimensional network material remains, the three-dimensional network material being formed of the respective protein films.

10. The method of claim 9, wherein said removing includes evaporation of the oil droplets, and the oil includes n-hexadecane or hexane.

11. The method of claim 9, further comprising grafting the three-dimensional network material onto an implant or transplant material.

12. The method of claim 9, further comprising using the three-dimensional network material as a precursor for tissue or cell growth.

13. The method of claim 9, further comprising providing the three-dimensional network material into a human or animal body.

14. The method of claim 1, wherein the respective protein films include multiple protein layers with water interposed between adjacent layers.

15. The method of claim 1, further comprising collecting the encapsulated oil droplets, wherein the collecting includes using surface-modified hydrophobic nylon fibers to remove the encapsulated oil droplets from water.

16. The method of claim 1, wherein the combining includes mixing bacterial cells with the oil, said bacterial cells producing the fibrillar proteins and the bacterial cells include *Bacillus subtilis*, and further comprising growing the bacterial cells to a late stationary phase prior to the mixing.

17. A method for oil spill clean-up from a body of water using a network material, the method comprising:
    selecting one of (a) a microbial entity that produces amyloids and (b) amyloids that are isolated from the microbial entity;
    adding the selected one to oil in or on said body of water such that the amyloids disperse the oil into droplets, each of which is encapsulated by an aggregate film,
    wherein the aggregate film consists essentially of multiple layers of the amyloids with water disposed between adjacent layers.

18. The method of claim 17, wherein the oil droplets have respective diameters in the range from 50 nm to 2 mm.

19. The method of claim 18, wherein at least some of the oil droplets have respective diameters of at least 1 µm.

20. The method of claim 17, wherein said oil includes crude oil, and the microbial entity is *Bacillus subtilis*.

21. The method of claim 17, further comprising:
    culturing the microbial entity to a late stationary phase; and
    harvesting and isolating the produced amyloids from the cultured microbial entity, wherein said selecting is for the isolated amyloids.

22. The method of claim 17, further comprising collecting the encapsulated oil droplets from the body of water.

23. The method of claim 22, further comprising contacting the aggregate films together so as to form a three-dimensional network material with the oil droplets stored in pockets within the network material.

24. The method of claim 22, wherein the collecting includes using surface-modified hydrophobic nylon fibers to remove the encapsulated oil droplets from the body of water.

* * * * *